United States Patent [19]
Lam et al.

[11] Patent Number: 5,137,900
[45] Date of Patent: Aug. 11, 1992

[54] THERAPEUTIC VIRGINIAMYCIN $M_1$ ANALOGS

[75] Inventors: Yiu-kuen T. Lam, Plainsboro, N.J.;
Raymond S. Chang, Lansdale, Pa.;
Otto D. Hensens, Red Bank, N.J.;
Cheryl D. Schwartz, Westfield, N.J.;
Deborah L. Zink, Manalapan, N.J.

[73] Assignee: Merck & Co., Inc., Rahway, N.J.

[21] Appl. No.: 644,755

[22] Filed: Jan. 23, 1991

Related U.S. Application Data

[60] Continuation of Ser. No. 365,402, Jun. 13, 1989, abandoned, which is a division of Ser. No. 934,212, Nov. 21, 1986, Pat. No. 4,859,690.

[51] Int. Cl.$^5$ .............................................. A61K 31/42
[52] U.S. Cl. ............................................................. 514/375
[58] Field of Search ........................................ 514/375

[56] References Cited
PUBLICATIONS

Microbiological Reviews, Jun. 1979, p. 145-198 "Cocito" Antibiotics of the Virginiamycin Family Inhibitor Which Contain Synergism Component.

*Primary Examiner*—Jerome D. Goldberg
*Attorney, Agent, or Firm*—Alice O. Robertson; Hesna J. Pfeiffer

[57] ABSTRACT

Virginiamycin $M_1$ having the Formula:

and virginiamycin $M_1$ analogs having the Formulae I-IV:

(List continued on next page.)

-continued (III)

(IV)

-continued

Virginiamycin $M_1$ and the analogs I–IV are antagonists of cholecystokinin (CCK) and gastrin. Cholecystokinin antagonists are useful as analgesics and in the treatment and prevention of disorders of the gastrointestinal, central nervous and appetite regulatory systems in animals, especially humans. Gastrin antagonists are useful in blocking the receptors for gastrin in humans and may function as agents for the treatment of ulcers, tumors or other gastrointestinal disorders. The compounds of Formulae I–IV are also antibiotics and are useful as antimicrobial agents in animals including man and are useful as food additives to promote feed utilization in animals. Virginiamycin $M_1$ and the analogs of Formula I, III and IV are produced by the controlled aerobic fermentation of a strain of *Streptomyces olivaceus*, ATCC No. 53527. The analog of Formula II is produced by chemical synthesis.

6 Claims, 4 Drawing Sheets

THERAPEUTIC VIRGINIAMYCIN M₁ ANALOGS

This is a continuation, of application Ser. No. 365,402, filed Jun. 13, 1989, now abandoned, which is a continuation of application Ser. No. 934,212, filed Nov. 21, 1986, now U.S. Pat. No. 4,859,690.

OBJECTS OF THE INVENTION

It is accordingly, an object of the present invention to provide virginiamycin M₁ and analogs which are CCK and gastrin antagonists. Another object is to provide novel analogs of virginiamycin M₁ with antibiotic activity. A further object is to provide a fermentation process for the preparation of virginiamycin M₁ and the analogs of Formulae I, III and IV. Another object is to provide a chemical process for the synthesis of compounds with the Formulae I, II and III. Still another object is to provide pharmaceutical compositions comprising virginiamycin M₁ and such analogs. Another object is to provide methods of treatment comprising administering virginiamycin M₁ and such analogs and compositions when an antibiotic, analgesic, antiulcer, or a therapeutic agent for gastrointestinal, central nervous and appetite regulatory system disorders is indicated. These and other objects of the present invention will be apparent from the following description.

SUMMARY OF THE INVENTION

Virginiamycin M₁ having the Formula:

and virginiamycin M₁ analogs having the Formulae I-IV:

Virginiamycin M₁ and the analogs I-IV are antagonists of cholecystokinin (CCK) and gastrin. Cholecystokinin antagonists are useful as analgesics and in the treatment and prevention of disorders of the gastrointestinal, central nervous and appetite regulatory systems in animals, especially humans. Gastrin antagonists are useful in blocking the receptors for gastrin in humans and may function as agents for the treatment of ulcers, or other gastrointestinal disorders. The compounds of Formulae I-IV are also antibiotics and are useful as antimicrobial agents in animals including man and are useful as food additives to promote feed utilization in animals.

BACKGROUND OF THE INVENTION

Cholecystokinin (CCK) and gastrin (G) are regulatory peptides which are found in gastrointestinal tissue and in the central nervous system, Mutt, *Gastrointestinal Hormones.* Glass, Ed. Raven Press, N.Y., p. 169 (1980). The CCK peptides reportedly co-exist with dopamine in certain mid-brain neurons, and thus may play a role in the functioning of dopaminergic systems in the brain, as well as serving as neurotransmitters, Prange et al., Ann. Repts. Med. Chem. 17: 31 (1982). Gastrointestinal CCK and gastrin may act on parietal and chief cells of the fundic glands of the mammalian gastric mucosa to stimulate acid and pepsinogen secretion, Chew and Hersey, Am. J. Physiol. 242: G504 (1982). Cholecystokinins are also believed to be physiological satiety hormones and, thus, may play a role in appetite regulation, Smith, *Eating and Its Disorders,* Stunkard and Steller, Eds., Raven Press, N.Y., p. 67 (1984). Additional effects of CCKs include the stimulation of colonic motility, gall bladder concentration, pancreatic enzyme secretion and the inhibition of gastric emptying.

Intestinal CCK exists in 39- and 33-amino acid forms with the C-terminal 33-amino acid residues being identical. Biological activity is restricted to the C-terminal heptapeptide of the native peptide and a C-terminal octapeptide has the same efficacy as CCK-33 but is approximately ten-times more potent, Jensen et al., Proc. Natl. Acad. Sci. USA 77: 2079 (1980).

Gastrin also occurs naturally in several different forms; 34-amino acids, 17-amino acids and 13-amino acids with the tyrosine being either sulfated or unsulfated. The 17- and 13-amino acid forms can be viewed as C-terminal fragments of the 34-amino acid form. The different forms exhibit varying potency for stimulating gastric acid secretion. Gastrin-17 is 5 times more potent than Gastrin-34 and 2.5 times more potent than Gastrin-13, Walsh and Grossman, New Engl. J. Med. 292: 1324,1377 (1975). Gastrin and CCK share a common C-terminal pentapeptide amide sequence, Gly-Trp-Met-Asp-Phe-$NH_2$.

Gastrin and CCK antagonists are useful for treating diseases mediated by gastrin and CCK. CCK antagonists are successful in preventing or treating CCK-related disorders of the gastrointestinal, central nervous and appetite regulatory systems of animals, especially of humans. Antagonists of CCK are also useful in potentiating and prolonging opiate-mediated analgesia and thus have utility in the treatment of pain, Faris et al., Science 226: 1215 (1984). Gastrin antagonists are useful in the treatment and prevention of gastrin-related disorders of the gastrointestinal system in humans and animals, such as ulcers, Zollinger-Ellison syndrome, antral G cell hyperplasia and other conditions, in which reduced gastrin activity is of therapeutic value. CCK and gastrin also have trophic effects on certain tumors, Ohyama, Hokkaido J. Med. Sci., 60, 206 (1985), and antagonists of CCK and gastrin may be useful in treating these tumors.

Antibiotics of the Virginiamycin family have been used as food additives to improve the growth of poultry, swine and cattle. Although growth promotion by antibiotics is not thoroughly understood, there is little doubt that the effect is due in part to an inhibition of the intestinal flora, Coccito, Micro. Rev. 43: 145 (1979). Virginiamycin $M_1$ and related antibiotics are generally specific for gram-positive bacteria and prevent cell multiplication. The virginiamycin antibiotics are most effective when in their complex form, that is when they are composed of both M and S components, Coccito, Micro. Rev. 43: 145 (1979). The wide use of these antibiotics as growth promoters relates their low toxicity, lack of accumulation in animal tissues, no production of resistant mutants and a rapid degradation in animal feces.

DETAILED DESCRIPTION OF THE INVENTION

Virginiamycin $M_1$ and the compounds of Formulae I, III and IV are produced by controlled aerobic fermentation of a strain of the *Streptomyces olivaceus*. It is to be understood that for the fermentation production of virginiamycin $M_1$ and the compounds of Formulae I, III and IV the present invention is not limited to the use of this specific species or strain of Streptomyces. It is especially desired and intended that there be included within the scope of this invention, the use of other natural or artificial mutants produced or derived from the described cultures, or other variants or species of the genus Streptomyces in so far as they can produce virginiamycin $M_1$ and the compounds of Formulae I, III and IV or any related analogs. The artificial production of mutant species or strains of this strain of Streptomyces may be achieved by conventional physical or chemical mutagens, for example, ultraviolet irradiation of the described cultures, or nitrosoguanidine treatment and the like. Recent recombinant DNA techniques such as plasmid incorporation in bacteria and fungi and the like may also prove useful.

Virginiamycin $M_1$ and the compounds of Formulae I, III and IV are produced by the controlled aerobic fermentation of a species of Streptomyces which has been deposited in the American Type Culture Collection, 12301 Parklawn Drive, Rockville, Md. 20852, USA, on Jul. 29, 1986, under the "Budapest Treaty on the International Recognition of the Deposit of Microorganisms for the Purposes of Patent Procedure" and has been assigned ATCC number 53527.

The Streptomyces species was isolated from soil associated with tree roots in Pimipri, India and expresses morphological and cultural characteristics as shown in the following table:

TABLE I

| Morphology: Sporophores from very loose coils, chains are more than 15 spores in length, spores are spherical to oval, and are about $0.9\mu$ to $0.9 \times 1.2\mu$ in size |
|---|

| Cultural Charastics: Yeast extract-malt extract agar (ISP Medium 2) | |
|---|---|
| V: | Reverse - grayish brown edged with gray |
| A: | Light gray mixed with white and edged with dark gray |
| SP: | None |
| Oatmeal agar (ISP Medium 3) | |
| V: | Reverse - light grayish tan edged with gray |
| A: | Light gray mixed with white, edged with dark gray |
| SP: | None |
| Inorganic salts-starch agar (ISP Medium 4) | |
| V: | Reverse - grayish tan edged with gray |
| A: | Light gray mixed with white, edged with dark gray |
| SP: | None |
| Glycerol asparagine agar (ISP Medium 5) | |
| V: | Reverse - tan edged with gray |
| A: | Light gray and white edged with light gray |
| SP: | None |
| Peptone-iron-yeast extract agar (ISP Medium 6) | |
| V: | Reverse - tan |
| A: | Pale gray mixed with white and edged with medium gray |
| SP: | None |
| Melanin: | None |
| Tyrosine Agar (ISP Medium 7) | |
| V: | Reverse - tan edged with brown |
| A: | Mixed grayish - white and gray edged with dark gray |
| SP: | Slight browning of medium |
| Czapek-Dox Agar | |
| V: | Reverse - grayish tan |
| A: | Light gray mixed with white |
| SP: | Slight browning of medium |

V = vegetative growth;
A = aerial mycelium;
SP = soluble pigment

Color number designations taken from Color Harmony Manual, 1958, 4th Edition, Container Corporation of America, Chicago, Ill.

The carbon utilization of ATCC 53527 was determined using Pridham-Gottlieb basal medium (ISP Medium 9) supplemental with 1% carbon sources as seen in the following table:

TABLE II

| Glucose | + | Mannitol | + |
|---------|---|----------|---|
| Arabinose | + | Mannose | + |
| Cellulose | − | Raffinose | ± |
| Fructose | + | Rhamnose | + |
| Inositol | + | Sucrose | + |
| Lactose | + | Xylose | + |
| Maltose | + | | |

[+ = growth; ± = growth poor or questionable; − = no growth as compared to negative control (no carbon source)]

The temperature growth range and oxygen requirements were determined using yeast extractdextrose+salts agar. The results are shown in the following table:

TABLE III

Temperature range
(Yeast extract-dextrose + salts agar)

| 28° C. | Good vegetative growth and sporulation |
|--------|----------------------------------------|
| 37° C. | Good vegetative growth and sporulation |
| 42° C. | No growth |
| 50° C. | No growth |

Oxygen requirements
(Stab culture in yeast extract-dextrose + salts agar)

Aerobic

All readings taken after three weeks at 28° C. unless noted otherwise. PH of all media approximately neutral (6.8–7.2).

The cultural characteristics of this organism are compared with culture descriptions of Streptomyces species described in Berger's Manual of Determinative Bacteriology, Eighth Edition, 1974, Williams & Wilkens, Baltimore, Md., and the Streptomeyces species is presumptively identified as a strain of *Streptomyces olivaceous*.

The fermentation is carried out at a temperature range of from about 20° C. to about 37° C., with 28° C. being preferred. Generally, the composition of the assimilable nutrient medium may be varied over a wide range. The essential nutrient ingredients are a carbon source and a nitrogen source. Other essential nutrients are provided via mineral salts such as chlorides, nitrates, sulfates, carbonates and phosphates of sodium, potassium, ammonium and calcium. The nutrient medium may also contain sources of inorganic trace elements such as magnesium, iron, copper, manganese, zinc, cobalt and the like.

Typical sources of carbon include; sugars, oils, organic acids, dextrin, starches, glycerol and the like. Typical nitrogen sources include; amino acids, vegetable meals, and extracts (e.g., malts, soy, cotton seed, figs, tomato, corn, etc.), animal viscera, various hydrolysates (e.g., casein, yeast, etc.) and industrial by-products such as lard water and distillers solubles.

The maximum yield of virginiamycin $M_1$ and the compounds of Formulae I, III and IV is achieved within about 24 to about 96 hours, usually in about 48 to about 72 hours, of fermentation under optimum conditions. The inoculum for the fermentation is provided from vegetative growth in a medium which supports rapid growth of the microorganism or by direct inoculation of frozen biomass.

The terms "seed" and "production" media are employed as terms of art. Generally, a seed medium supports rapid growth of the microorganism and an aliquot (seed) of this medium is used to inoculate a production medium for a large scale fermentation.

Following fermentation, the accumulated virginiamycin $M_1$ and the compounds of Formulae I, III and IV are recovered from the culture broth by conventional chromatographic means. The individual compounds are separated by reverse phase high performance chromatography.

Virginiamycin $M_1$ and the compounds of Formulae I, III and IV are isolated from whole fermentation broth by the addition of a nearly equal volume of a moderately polar solvent immiscible in water. Such solvents include chloroform, ethyl acetate, methyl ethyl ketone and the like, with methyl ethyl ketone being preferred. The layers are allowed to settle and the organic layer collected. The organic layer contains virginiamycin $M_1$ and the compounds of Formulae I, III and IV.

Isolation of the various compounds from the fermentation broth is based on specific biological activity. The products resulting from the chemical conversion of virginiamycin $M_1$ to compound III and subsequently to compounds I and II are also assayed for biological activity. The biological assays include gastrin binding to mammalian gastric glands, preferably guinea pig and CCK binding to mammalian brain, preferably guinea pig or mammalian pancreas, preferably rat.

The active organic layer isolated from the culture broth was flash evaporated under reduced pressure at a temperature of about 30° C. to about 50° C., with 40° C. being preferred, and partitioned between a saturated hydrocarbon such as hexane and an alcohol such as methanol. The methanol layer is flash evaporated at about 30° C. to about 50° C., with 40° C. being preferred, under pressure and chromatographed on silica gel using a mobile phase of acetone about 50% to about 75% in hexane. The active fraction was purified by reverse phase high performance liquid Chromatography (HPLC).

Virginiamycin $M_1$ is converted to the compound of Formula III by the addition of about 1 mole equivalent of methanesulfonyl chloride to an anhydrous pyridine solution of virginiamycin $M_1$. The mesylation reaction is allowed to proceed at about 25° C. for about 20 minutes and the pyridine is removed by flash evaporation. The residue is partitioned in about 1% aqueous NaCl and dichloromethane. The organic layer is then dried and chromatographed by reverse phase HPLC. The compound of Formula III is reduced to the compounds of Formulae II and I by sodium borohydride reduction. To a methanolic solution of the compound of Formula III is added a slight excess of 1 mole equivalent of a $NaBH_4$/methanol solution at about 10 mg/ml. Purification is similar to that for the fermentation products.

Biological activity of virginiamycin $M_1$ and the compounds of Formulae I, II, III and IV is determined by gastrin receptor binding, pancreas CCK receptor binding, brain CCK binding and microbial growth inhibition assays.

Virginiamycin $M_1$ and the compounds of Formulae I, II, III and IV can be administered to mammals, including humans, either alone, or preferably, in combination with pharmaceutically acceptable carriers or diluents, in a pharmaceutical composition, according to standard pharmaceutical practice. The compounds can be administered orally or parenterally. Parenteral administration includes intravenous, intramuscular, intraperitoneal, subcutaneous, and topical administration.

For oral use as CCK or gastrin antagonists or as antibiotics, the selected compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. For oral use as antibiotics in domestic animals, the compounds of Formulae I, II, III, and IV are added to the animal feed. If desired, certain sweetening and/or flavoring agents can be added. For intramuscular, intraperitoneal, subcutaneous, and intravenous use, sterile solutions of the active ingredient are usually prepared, and the PH of the solutions should be suitably adjusted and buffered. For intravenous use, the total concentration of solutes should be controlled to render the preparation isotonic.

When virginiamycin $M_1$ and the compounds of Formulae I, II, III, and IV are used as a CCK or gastrin antagonist or an antibiotic in a human subject, the daily dosage will normally be determined by the prescribing physician. Moreover, the dosage will vary according to the age, weight, and response of the individual patient, as well as the severity of the patient's symptoms. However, in most instances, an effective daily dosage will be in the range from about 1 mg to about 1500 mg and preferably 10 mg to 500 mg in a single or divided doses. On the other hand, it may be necessary to use dosages outside these limits in some cases.

When the compounds of Formulae I, II, III, and IV are used as an oral antibiotics for domestic animals, the daily dosage will be determined according to the age, weight, and species of animal being treated. The effective dosage will be in the range from about 5 to about 200 parts per million per volume of food.

Virginiamycin $M_1$ and the compounds of Formulae I, II, III and IV bind to both CCK and gastrin receptors. Thus, virginiamycin $M_1$ and the four analogues may have a unique function in appetite regulation, the treatment of CCK-related disorders of the gastrointestinal and central nervous system. The unique action of virginiamycin $M_1$ and the four analogues as gastrin antagonists will allow their use in the treatment and prevention of gastrin-related disorders such as ulcers, Zollinger-Ellison syndrome and antral G cell hyperplasia. The four analogs also function as antibiotic agents and can be used to treat microbial infections.

The following examples illustrate the present invention without, however, limiting the same thereto.

EXAMPLE 1

Fermentation

A lyophilized tube of the Streptomyces ATCC No. 53527 was added under aseptic conditions to 54 ml of a seed medium in a 250 ml baffled Erlenmeyer flask. The seed media contained the following: dextrose, 1 gm/L; soluble starch, 10 g/L; beef extract, 3 g/L; ardamine PH, 5 g/L; NZ amine, 5 g/L; $MgSO_4.7H_2O$, 0.08 g/L; phosphate buffer, 2 ml/L and $CaCO_3$, 0.5 g/L. The pH of the medium was between 7.0 and 7.2. The flask was maintained at 28° C. on a 220 rpm rotary shaker for 48 hours. Ten ml of the 48 hour culture was aseptically transferred to 500 ml in a 2 L baffled flask and incubated at 28° C. on a 220 rpm rotary shaker for 24 hours. A 500 ml inoculum from the second seed culture was added to 10 L of production medium in a 14 L fermenter. The production media contained corn gluten meal, 5.0 g/L; Primatone HS, 2.5 g/L; yeast extract (Fidco), 1.0 g/L; malt extract, 10.0 g/L; sucrose, 5.0 g/L; $CaCO_3$, 5.0 g/L and P-2000, 2.0 ml. The pH of the production medium was between 7.2 and 7.4. The inoculated production media was incubated for 64 hours at 28° C., aerated at a flow of 3 L per minute and agitated at 400 rpm.

EXAMPLE 2

Isolation and Characterization of Virginiamycin $M_1$ and Compounds of the Formulae I. III and IV Forty L of whole culture broth from Example 1 was extracted with 48 L of methylethyl ketone. The organic layer contained the biological activity and was flash evaporated under reduced pressure at 40° C. to give a residue. The residue was partitioned between hexane, 1 L, and methanol, 1 L, with the hexane layer being discarded. The active methanol layer was flash evaporated under reduced pressure at 40° C. to yield a 50 g dry weight sample. Flash chromatography of this material in 5 runs on 500 g silica gel 60 (4 μm) using 50% acetone/hexane and then 75% acetone/hexane as the mobile phases yielded active fractions with a total dry weight of 3 grams. Subsequent preparative reverse phase high performance liquid chromatography of this material in 3 runs on a Zorbax C-8, 2.12×25 cm, column using 40% acetonitrile/water as the isocratic mobile phase at room temperature and 15 ml/min yielded 92 mg of virginiamycin $M_1$; 5.2 mg of the compound of Formula I; 16.4 mg of the compound of Formula III and 25.9 mg of the compound of Formula IV.

Physiochemical characterization of the virginiamycin $M_1$ isolated from the present fermentation was identified by comparison with EI-MS and $^1H$-NMR data ($M^+ = 525$) from the literature, Kingston et al., J. Chem. Soc. 19: 1669-1676 (1966), and an authentic sample obtained by purifying a commercially available virginiamycin. Subsequent biological/biochemical testing on virginiamycin $M_1$ was performed on this authentic sample. Both samples showed identical HPLC retention times and UV spectra ($\lambda_{max}=210.5$ nm; $E\%=535$). A 300 MHz $H^1$—$H^1$ homonuclear correlation NMR spectrum was recorded for the first time for characterization.

Figure 1:
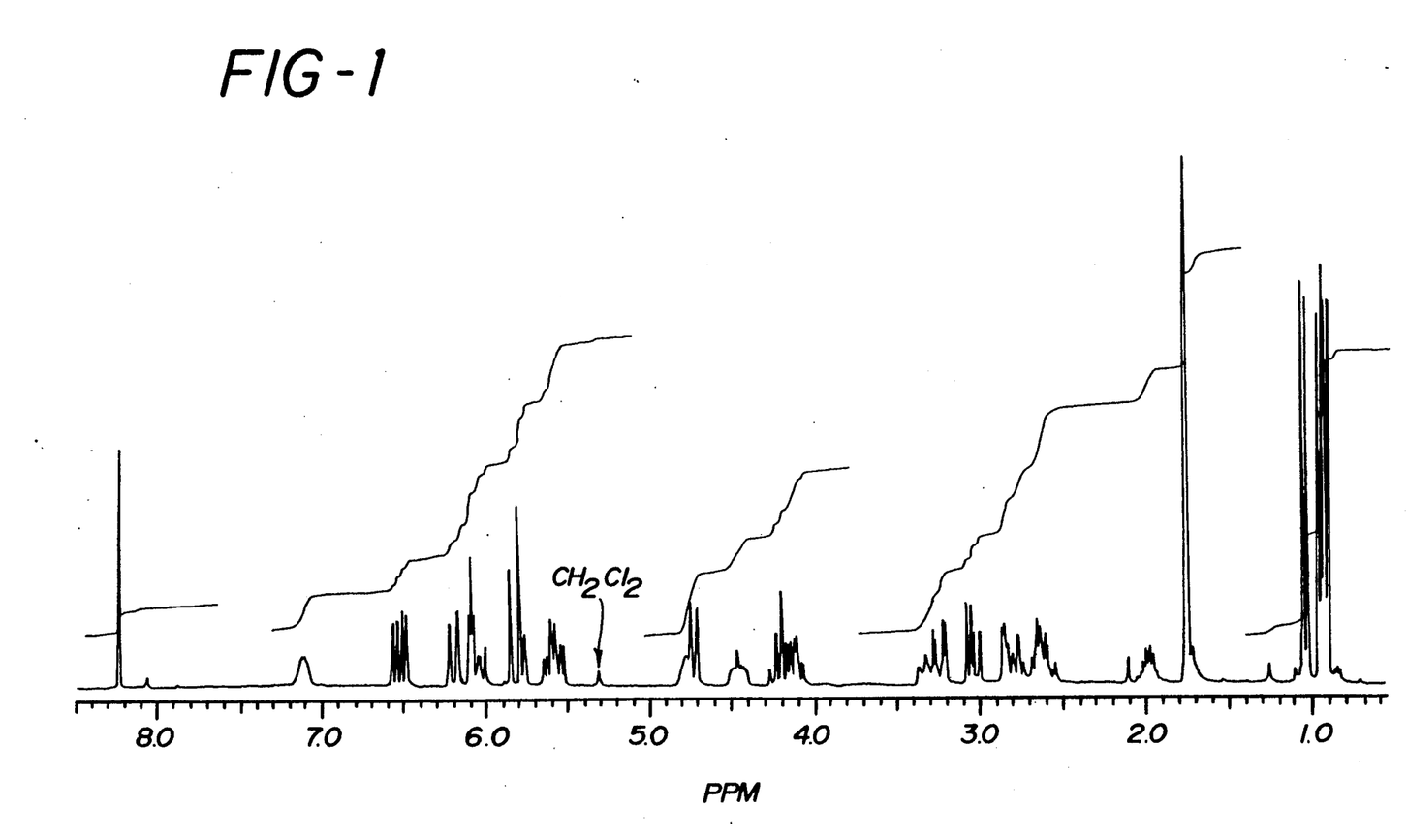
FIG. 1 is a H¹-nuclear magnetic resonance (NMR) spectrum of the compound of Formula I.
Figure 3:
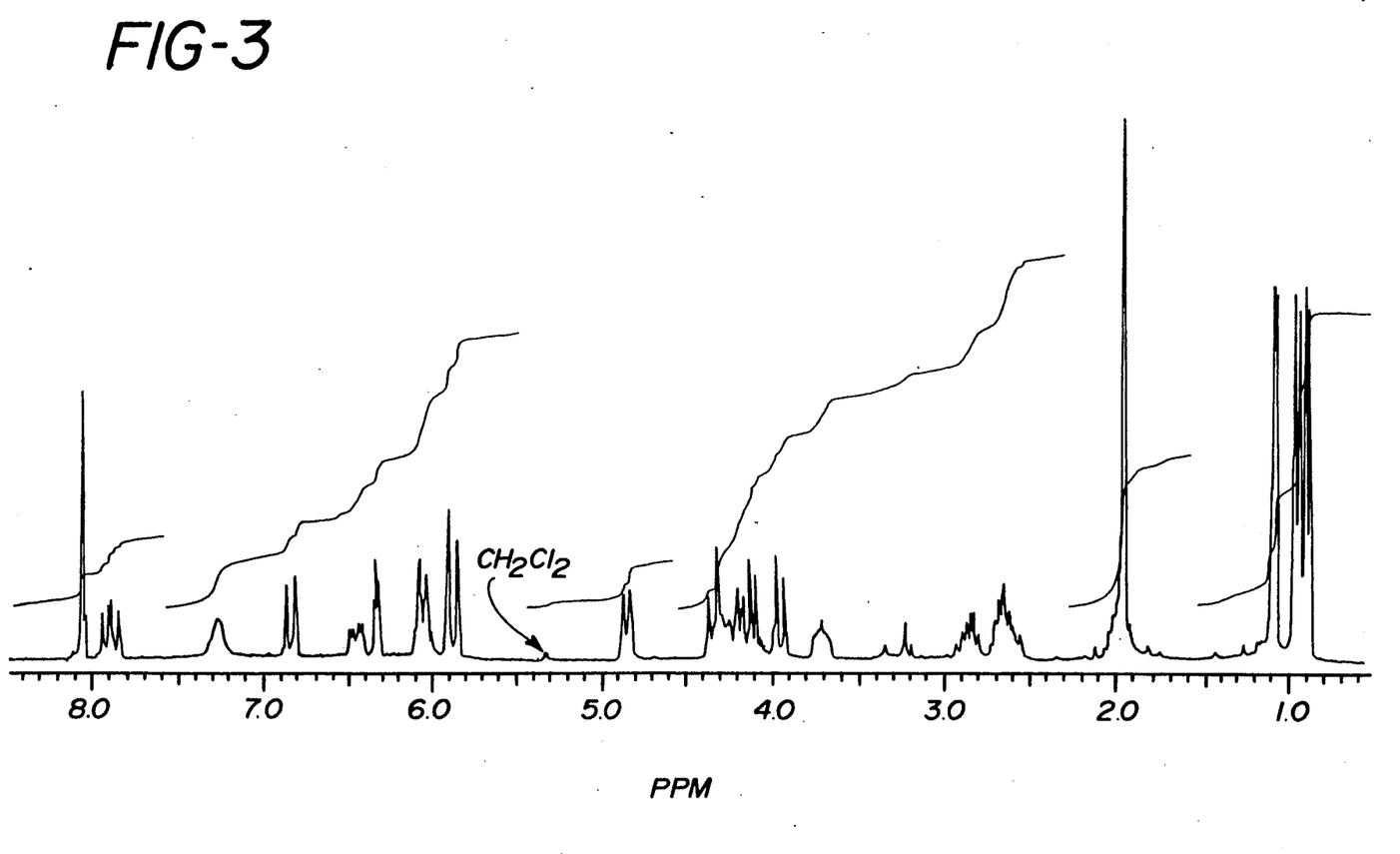
FIG. 3 is a H¹-nuclear magnetic resonance (NMR) spectrum of the compound of Formula III.
Figure 4:
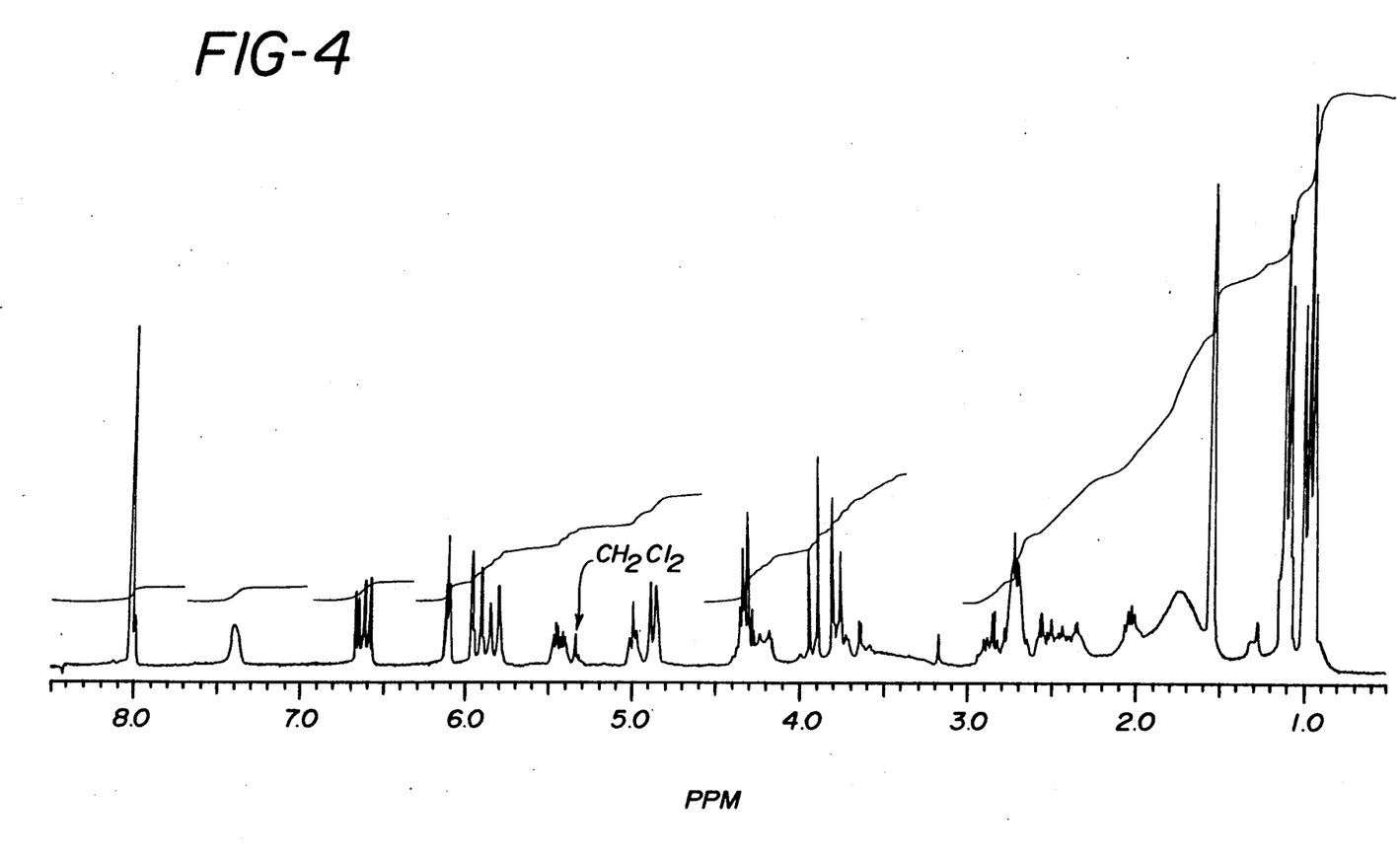
FIG. 4 is a H¹-nuclear magnetic resonance (NMR) spectrum of the compound of Formula IV.

High resolution mass spectral data of the compound of Formula I revealed a molecular formula of $C_{28}H_{35}N_3O_6$ (calculated: 509.2526; found: 509.2528). Its 300 MHz $H^1$-NMR spectrum, see FIG. 1, in $CD_2Cl_2$ further corroborated the purity and identity of this compound. Broad band decoupled $C^{13}$-spectrum in $CD_2Cl_2$ revealed resonances at 12.11; 18.82; 19.77; 20.34; 29.91; 30.13; 36.77 38.87; 42.26; 51.08; 70.93; 82.46; 123.77; 123.85; 125.78; 126.46; 127.11; 127.72; 129.20; 132.85; 132.93; 135.20; 137.13; 143.29; 143.58; 161.37; 161.86; 167.13 ppm. Its ultraviolet spectrum in methanol displayed absorption maxima at 212 nm ($E\%=557$) and 274.5 nm ($E\%=764$). Its infrared spectrum in $CH_2Cl_2$ solution showed absorption bands at 3595; 3375; 1730; 1670 and 1620 cm$^{-1}$. The natural and semisynthetic compound, Example 4, showed identical mass, $H^1$-NMR, and UV spectra, and HPLC retention time and allowed the assignment of the following structure:

High resolution mass spectral data for the compound of Formula III revealed a molecular formula of $C_{28}H_{33}N_3O_6$ (calculated: 507.2369; found: 507.2369). Its 300 MHz $H^1$-NMR spectrum, see FIG. 3, in $CD_2Cl_2$ further corroborated the purity and identity of this product. Its broad band decoupled $C^{13}$-NMR spectrum in $CD_2Cl_2$ revealed resonances at 12.19; 18.78; 1960; 21.37; 30.10; 30.22; 37.60; 40.65; 42.04; 52.33; 81.18; 125.38; 126.56; 126.79; 127.25; 129.46; 131.85; 136.98; 142.91; 143.20; 143.32; 146.19; 160.28; 160.54; 167.12; and 192.78 ppm. Its ultraviolet spectrum in methanol displayed absorption maxima at 212 nm (E%=545.5) and 325 nm (E%=417). Its infrared spectrum in $CH_2Cl_2$ solution showed absorption bands at 3380; 1730; 1662 and 1625 cm$^{-1}$. The natural and semisynthetic compound, Example 3, showed identical mass, $H^1$-NMR, and UV spectra, and HPLC retention time and allowed the assignment of the following structure:

High resolution mass spectral data for the compound of Formula IV on the bis-trimethylsilyl derivative revealed a molecular formula of $C_{28}H_{35}N_3O_6+T_2$ (calculated 653.3316; found: 653.3452). Its 300 MHz $H'$-NMR spectrum, see FIG. 4, in $CD_2Cl_2$ further corroborated the purity and identity of this product. Its ultraviolet spectrum in methanol is almost identical to that of Virginiamycin $M_1$ and displayed an absorption maximum at 213 nm (E%=542) and allowed the assignment of the following structure:

EXAMPLE 3

Synthesis of the Compound of Formula III

Virginiamycin $M_1$, from Example 2 or obtained commercially, was converted to the compound of Formula III by adding methanesulfonyl chloride, 0.2 ml, to 199.36 mg of virginiamycin $M_1$ in anhydrous pyridine solution, 5 ml. The mesylation reaction was allowed to proceed at room temperature for 20 minutes. Flash evaporation of the solvent, pyridine, under reduced pressure and at 40° C. gave a residue. Partition of this residue in 1% aqueous NaCl, 20 ml, and dichloromethane (2×25 ml) followed by drying the organic layers in anhydrous $Na_2SO_4$ and flash removal of solvent under reduced pressure and at 40° C. yielded 245 mg of a crude product. Analytical high performance liquid chromatography of this product revealed the presence of compound III as the predominant product and the absence of virginiamycin $M_1$. Preparative reverse phase chromatography of the crude product on a Zorbax ODS column with 40% aqueous MeCN as the mobile phase at 15 ml/minutes provided 88.15 mg of pure compound III.

EXAMPLE 4

Synthesis of Compounds of the Formulae I and II

Compound III was converted to compounds of the Formulae I and II. To a methanolic solution, 10 ml of compound III, from Example 1 or Example 3, was added 0.5 ml of a 10 mg/ml $NaBH_4/MeOH$ solution. High pressure liquid chromatographic analysis of the reaction mixture revealed that the reaction was immediate and the products were compound I and its epimer, compound II. The reaction was then worked up. The addition of acetone, 0.1 ml, to the reaction mixture destroyed any excess reagent. Partition of the mixture between 1% aqueous NaCl, 50 ml, and $CH_2Cl_2$, 2×50 ml, followed by drying the organic layers in anhydrous $Na_2SO_4$ and flash evaporation under reduced pressure at 30° C. afforded 54.8 mg material. Purification of this material on a preparative Zorbax ODS column, 2.12×25 cm, with 35% aqueous MeCN as the isocratic mobile phase at 15 ml/min at room temperature yielded 27.69 mg of Compound I and 15.7 mg of its epimer, compound of the Formula II.

Figure 2:
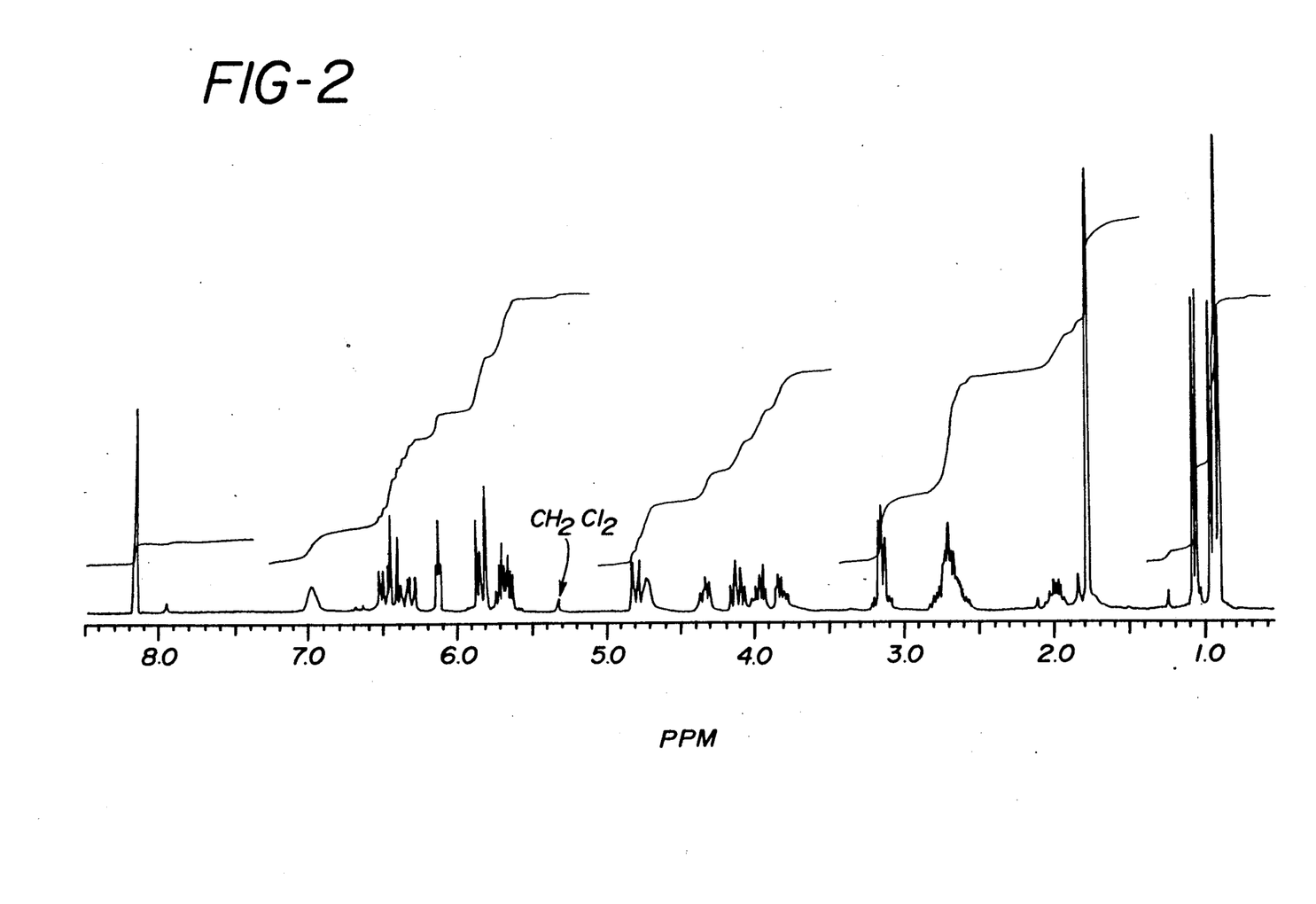
FIG. 2 is a H¹-nuclear magnetic resonance (NMR) spectrum of the compound of Formula II.

The physiochemical characterization of the compound of Formula I is presented in Example 2:

High resolution mass spectral data for the compound of Formula II revealed a molecular formula of $C_{28}H_{35}N_3O_6$ (calculated: 509.2526; found: 509.2528). Its 300 MHz $H^1$-NMR spectrum, see FIG. 2, in $CD_2Cl_2$ further corroborated the purity and identity of this compound. Its broad band decoupled $C^{13}$-NMR spectrum in $CD_2Cl_2$ revealed resonances at 12.03; 18.83; 19.67; 20.47; 30.07; 35.95; 39.10; 42.06; 51.04; 69.88; 81.75; 124.39; 124.47; 125.52; 126.98; 127.51; 127.57; 129.60; 129.62; 132.61; 135.19; 137.19; 143.22; 143.50; 161.23; 161.90 and 167.04 ppm. Its ultraviolet spectrum in methanol displayed absorption maxima at 212 nm (E%=522) and 274.5 nm (E%=701). Its infrared spectrum in $CH_2Cl_2$ solution showed absorption bands at 3600, 375; 1730; 1670 and 1625 cm$^{-1}$. These characteristics allowed the assignment of the following structure:

EXAMPLE 5

Gastrin Receptor Binding in Guinea Pig Gastric Glands

Guinea pig gastric mucosal glands were prepared by the procedure of Praissman et al., J. Receptor Res. 3:647 (1983). Stomachs from male Hartley guinea pigs (250–400 g body weight) were washed thoroughly and minced with fine scissors in HEPES buffer consisting of the following: 130 mM NaCl, 12 mM NaHCO$_3$, 3 mM NaH2PO$_4$, 3 mM Na$_2$HPO$_4$, 3 mM K$_2$HPO$_4$, 2 mM MgSO$_4$, 1 mM CaCl$_2$, 4 mM glucose and 4 mM L-glutamine, 25 mM HEPES at PH 7.4. The minced tissues were washed and incubated in a 37° C. shaker bath for 40 minutes, with HEPES buffer containing 0.1% collagenase and 0.1% bovine serum albumin (BSA), and bubbled with 95% O$_2$ and 5% CO$_2$. The tissues were passed twice through a 5 ml glass syringe to liberate the gastric glands, and then filtered through 200 mesh nylon. The filtered glands were centrifuged at 270×g for 5 minutes and washed twice by resuspension and centrifugation.

The washed guinea pig gastric glands were resuspended in 25 ml of HEPES buffer containing 0.25 mg/ml of bacitracin. For binding studies, 14.2 μl of 50% MeOH/H$_2$O (for total binding) or gastrin (1 μM final concentration, for nonspecific binding) or broth or test compound from Examples 2, 3 or 4 and 20 μl of $^{125}$I-gastrin (New England Nuclear [NEN], 20,000 cpm 20 μl) were added to 220 μl of gastric glands in triplicate tubes which were aerated with 95% O$_2$ and 5% CO$_2$ and capped. The reaction mixtures, after incubation at 25° C. for 30 minutes in a shaking water bath, were filtered under reduced pressure on glass. GF/B filters (Whatman) and immediately washed with 3×4 ml of HEPES buffer containing 0.1% BSA fraction V. The radioactivity on the filters was measured using a Beckman 5500 gamma counter for $^{125}$I-gastrin.

The results of the gastrin binding assay are shown in the following table:

TABLE IV

| Gastrin Receptor Binding | |
|---|---|
| Compound | IC$_{50}$ (nM) |
| Virginiamycin M$_1$ | 710 |
| I | 12 |
| II | 13 |
| III | 90 |
| IV | 360 |

EXAMPLE 6

Pancreatic Cholecystokinin Receptor Binding Assay

Radiolabeled CCK-8 was purchased from New England Nuclear as $^{125}$I-CCK-8 Receptor binding was performed according to Innis and Snyder Proc. Natl. Acad. Sci., 77, 6917 (1980), with the minor modification of adding the additional protease inhibitors, phenylmethane sulfonyl fluoride (PMSF) and o-phenanthroline, which have no effect on the $^{125}$I-CCK receptor binding assay. All assays were performed in triplicate. Pancreatic receptor membranes were prepared by homogenzing a gram of fresh rat pancreas tissue in 30 ml TRIS-HCl (50 mM), pH 7.7 using a Brinkman polytron PT10 (Brinkman). The homogenate was washed twice and collected by centrifugation at 48,000×g at 4° C. for 10 minutes. The membranes were resuspended in assay buffer consisting of 5 mM dithiothieitol, 0.1 mM bacitiacin, 5 mM MgCl$_2$.H$_2$O, 0.2% heat denatured BSA, 1.2 mM PMSF and 0.5 mM O-phenanthroline at a concentration of 100 ml per gram of pancreas. To each incubation tube, in an ice-bath, containing 0.45 ml of membrane preparation, 25 μl of assay buffer (for total binding) or unlabeled CCK 26-33 (for non-specific binding) or broth or test compound from Examples 2, 3 or 4 for determining the inhibition of specific CCK binding by broths, and 25 μl of $^{125}$I-CCK were added. The reaction mixtures were mixed briefly and placed in a 37° C. water bath with gentle shaking for 30 minutes. The reaction mixtures were then diluted with 4 ml of ice-cold TRIS buffer, pH 7.7, containing 1 mg/ml bovine serum albumin and immediately filtered in Watman G F/B filters. The filters were washed with 3×4 ml of the same buffer and the radioactivity associated with the filters was counted in a Beckman Gamma 5500 counter. Broths were prepared by adding two volumes of acetone to original broth; supernatants were freeze dried after centrifugation at 1500 g for 10 minutes. The dried samples were then brought up in methanol/H$_2$O (1:1) and ready for assay.

The results of the pancreatic CCK binding assay are shown in the following table:

TABLE V

| Pancreatic CCK Receptor Binding | |
|---|---|
| Compound | IC$_{50}$ (nM) |
| Virginiamycin M$_1$ | >100,000 |
| I | >10,000 |
| II | >10,000 |
| III | >10,000 |

EXAMPLE 7

Brain Cholecystokinin Receptor Binding Assay

CCK-8 binding was performed according to the description for the pancreatic method, with modifications by Saito et al., J. Neurochem., 37, 483 (1981).

The brains from male Hartley guinea pigs (300–500 g) were removed and placed in ice-cold 50 mM Tris HCl plus 7.58 g/L Trizma-7.4 [pH 7.4 at 25° C.]. The cerebral cortex was dissected and used as a receptor source and each gram of fresh guinea pig brain tissue was homogenized in 10 ml of Tris/Trizma buffer, pH 7.4, with a Brinkmann polytron PT-10. The homogenates were centrifuged at 42,000×g for 15 minutes, then the resulting pellets were resuspended in 200 volumes of binding assay buffer (10 mM N-2-hydroxy-ethyl-piperazine-N'-2-ethane-sulfonic acid (HEPES), PH 7.7 at 25° C., mM MgCl$_2$, 1 mM ethylene glycol-bis-(β-amino-ethyl-ether-N,N'-tetraacetic acid (EGTA), 0.4% BSA and 0.25 mg/ml bacitracin, pH 6.5).

The remainder of the binding assay method was as described for the pancreatic method, Example 6, except that the reaction mixtures were incubated at 25° C. for 2 hours before filtration and the filters were washed with HEPES buffer.

The results of the brain CCK binding assay are shown in the following table:

TABLE VI

| Brain CCK Receptor Binding | |
|---|---|
| Compound | IC$_{50}$ (nM) |
| Virginiamycin M$_1$ | 571 |
| I | 7.8 |
| II | 6.1 |
| III | 13.3 |
| IV | 270 |

EXAMPLE 8

Antibiotic Activity

The compounds of Formulae I, II, and IV and virginiamycin M$_1$ from Example 2 were assayed for antibiotic activity following a method described by Matsen and Barry, *Manual of Clinical Microbiology*, Lennette, Spaulding, and Truant, Eds., American Society for Microbiology, Washington, D.C., p. 418 (1974). The minimal inhibitory concentrations (MIC) were determined by applying serial dilutions of the compounds of Formulae I, III, and IV and virginiamycin M$_1$ to standard filter paper discs. The concentration of the test compounds ranged from 0.05 μg to 3.0 μg per disc in 20 μl of diluent. The test organism, *Micrococcus luteus*, was innoculated on the surface of an agar based nutrient medium in petri plates and the discs placed on the surface of the medium. The nutrient media consisted of nutrient broth supplemented with 0.2% yeast extract and 1.5% agar. The innoculated plates were incubated for 15 hours at 28° C. and the zones of inhibition determined. The MIC of each compound was determined by the method described in Matsen and Barry, supra. The results are shown in the following table:

TABLE IV

| Minimal Inhibitory Concentration | |
|---|---|
| Compound | MIC (μM) |
| Virginiamycin M$_1$ | 1.5 |
| I | 90.0 |
| III | 250.0 |
| IV | 15.0 |

What is claimed is:

1. A method of treating bacterial infections in mammals which comprises orally or parenterally administering to said mammals an antibacterially effective amount of a compound of the Formula I:

2. A method of treating bacterial infections in mammals which comprises orally or parenterally administering to said mammals an antibacterially effective amount of a compound of the Formula II:

3. A method of treating bacterial infections in mammals which comprises orally or parenterally administering to said mammals an antibacterially effective amount of a compound of the Formula III:

4. A method of treating bacterial infections in mammals which comprises orally or parenterally administering to said mammals an antibacterially effective amount of a compound of the Formula IV:

5. A method of treating bacterial infections in mammals which comprises orally or parenterally administering to said mammals an antibacterially effective amount of one or more of the compounds of the formula:

-continued or

6. A method of treating bacterial infections in mammals which comprises orally or parenterally administering to said mammals an antibacterially effective amount of one or more of the a compounds of:

Formula I,

Formula III, or

Formula IV,

* * * * *